United States Patent [19]

Masaki

[11] Patent Number: 4,960,124

[45] Date of Patent: Oct. 2, 1990

[54] DEVICE FOR LOW-FREQUENCY ELECTROTHERAPY

[75] Inventor: Kazumi Masaki, Osaka, Japan

[73] Assignee: Ken Hayashibara, Okayama, Japan

[21] Appl. No.: 346,310

[22] Filed: May 1, 1989

Related U.S. Application Data

[63] Continuation of Ser. No. 89,952, Aug. 26, 1987, abandoned.

[30] Foreign Application Priority Data

Aug. 31, 1986 [JP] Japan ................. 61-133325

[51] Int. Cl.⁵ .............................. A61N 1/32
[52] U.S. Cl. ................. 128/421; 128/422; 331/112; 331/113 R
[58] Field of Search ............... 128/365, 366, 367, 368, 128/369, 370, 421, 422; 331/46, 47, 48, 49, 50, 51, 52, 53, 54, 55, 56, 106, 111, 112, 113 R, 143, 144, 146

[56] References Cited

U.S. PATENT DOCUMENTS

| | | | |
|---|---|---|---|
| 3,986,144 | 10/1976 | Russo | 331/113 R X |
| 4,249,537 | 2/1981 | Lee et al. | 128/422 |
| 4,372,319 | 2/1983 | Ichinomiya | 128/421 |
| 4,446,870 | 5/1984 | Wing | 128/422 |
| 4,535,777 | 8/1985 | Castel | 128/421 |

FOREIGN PATENT DOCUMENTS

| | | |
|---|---|---|
| 0033747 | 8/1981 | European Pat. Off. . |
| 0160753 | 4/1984 | European Pat. Off. . |
| DT. 2721757 | 11/1977 | Fed. Rep. of Germany . |
| DE. 2631472 | 1/1978 | Fed. Rep. of Germany . |
| DE. 3008351 | 9/1981 | Fed. Rep. of Germany . |
| 2267121 | 11/1975 | France . |

*Primary Examiner*—Steven L. Stephan
*Assistant Examiner*—Emanuel Todd Voeltz
*Attorney, Agent, or Firm*—Browdy and Neimark

[57] ABSTRACT

A device for low-frequency electrotherapy wherein the output current of a low-frequency oscillator is applied to the subject's body through a pair of electrodes placed on the subject's body, comprising a first oscillator circuit that generates a low-frequency square wave voltage when the load is in connection with the electrode pair; and a second oscillator circuit that generates a therapeutic voltage when the output voltage of the first oscillator circuit is not zero.

8 Claims, 3 Drawing Sheets

DEVICE FOR LOW-FREQUENCY ELECTROTHERAPY

This application is a continuation of application Ser. No. 07/089.952, filed Aug. 26, 1987.

BACKGROUND OF THE INVENTION

1. Field of the invention

The present invention relates to a device for low-frequency electrotherapy.

2. Description of the prior art

Although low-frequency electrotherapy usually requires application of a relatively high therapeutic voltage to realize strong muscle contraction and relaxation, it is favorable to apply a relatively low therapeutic voltage with appropriate interruptions because application of an excessively high therapeutic voltage may cause pain.

Conventional hand device using a battery has the drawback that discharge of the battery continues if the subject forgets to switch it off. In such a device, it is desirable to provide means for automatically turning off the power switch when the device is not in use.

SUMMARY OF THE INVENTION

In view of the foregoing, the main object of the present invention is to provide means wherein the drawbacks of a conventional device is overcome.

This and other objects may become apparent hereinafter as attained by the device for low-frequency electrotherapy wherein the output current of a low-frequency oscillator is applied to the subject's body through a pair of electrodes placed on the subject's body, characterized in that said low-frequency oscillator comprises a first oscillator circuit generating a low-frequency square wave voltage when the load is in connection with the electrode pair: and a second oscillator circuit generating a therapeutic voltage when the output voltage of the first oscillator circuit is not zero.

BRIEF DESCRIPTION OF THE DRAWINGS

The present invention will hereinafter be explained with reference to the accompanying drawings, in which.

DESCRIPTION OF THE PREFERRED EMBODIMENTS

Figure 1:
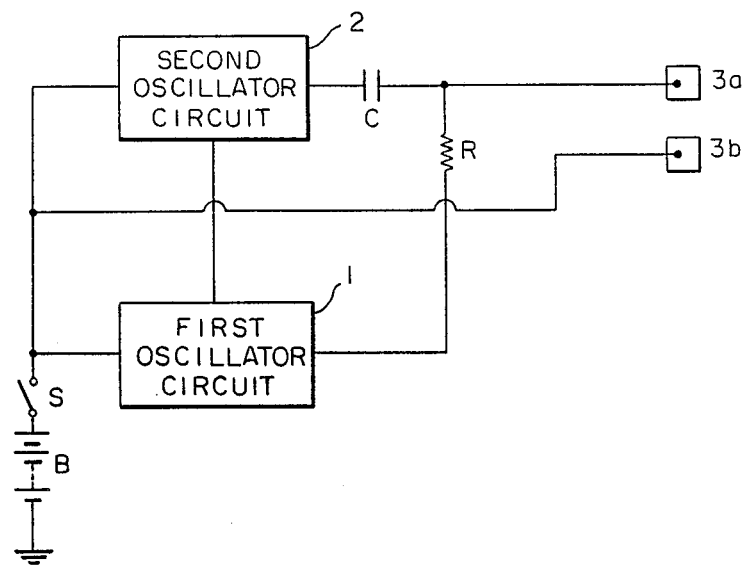
FIG. 1 is the block diagram of the device according to the invention.

Throughout the drawings, reference numeral (1) designates the first oscillator circuit; (2), the second oscillator circuit; (3a) and (3b), electrodes; symbol T, transistor; S, switch: C, capacitor; R, resistor: VR, variable resistor; H, transformer: and D, diode.

FIG. 1 is the block diagram of the device according to the invention. The device is arranged in such manner that battery B energizes first oscillator circuit (1) generating a low-frequency square wave, second oscillator circuit (2) generating a therapeutic voltage, and electrode (3b). Electrode (3a) is connected with the output terminal of second oscillator circuit (2) through the input terminal of first oscillator circuit (1) and capacitor C, while second oscillator circuit (2) is connected with the output terminal of first oscillator circuit (1). First oscillator circuit (1) is actuated by battery B when electrode pair (3a)(3b) are in connection with a load such as the subject's body. Second oscillator circuit (2) generates a therapeutic voltage when the voltage from first oscillator circuit (1) is not zero.

By setting the frequency of first oscillator circuit (1) to an appropriate level to optimize the conduction and interruption durations of second oscillator circuit (2), strong muscle contraction and relaxation can be attained by applying a relatively low therapeutic voltage.

Discharge of battery B is automatically suspended if the subject forgets to switch it off because first oscillator circuit (1) is actuated only when electrode pair (3a)(3b) is in connection with a load such as the subject's body.

Any low-frequency oscillator circuit can be used as first oscillator circuit (1) as far as it generates a low-frequency square wave. Specifically, oscillator circuits generating a square wave voltage of a frequency of 0.1–2 hertz, a vibration frequency inherent to the muscle, is preferable because it leads to appropriate conduction and interruption durations and attains painless, strong, natural muscle contraction and relaxation when used in combination with second oscillator circuit (2).

Examples of second oscillator circuit (2) include those that generate a low-frequency voltage of, for example, diphasic action potential wave, square wave, pulse wave, sinusoidal wave, semicircular wave, and exponential wave, and the voltage attains muscle contraction and relaxation when used in the device according to the invention. The most desirable waveform is the diphasic action potential wave as disclosed in Japanese Patent Publication No. 41,747/84 because it is superiorly effective in massaging the muscle, as well as relieving muscular fatigue.

Figure 3:
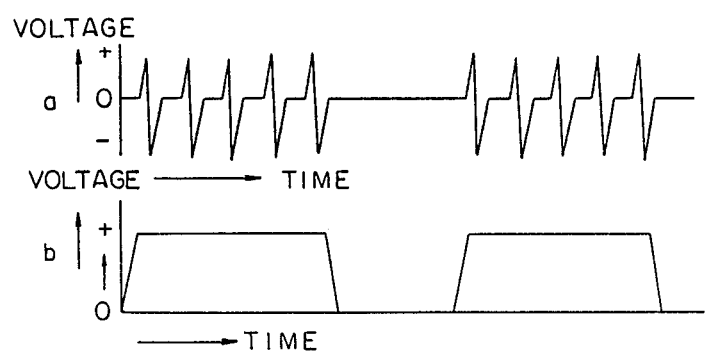
FIG. 3, the output waveforms appearing in the embodiment.
Figure 2:
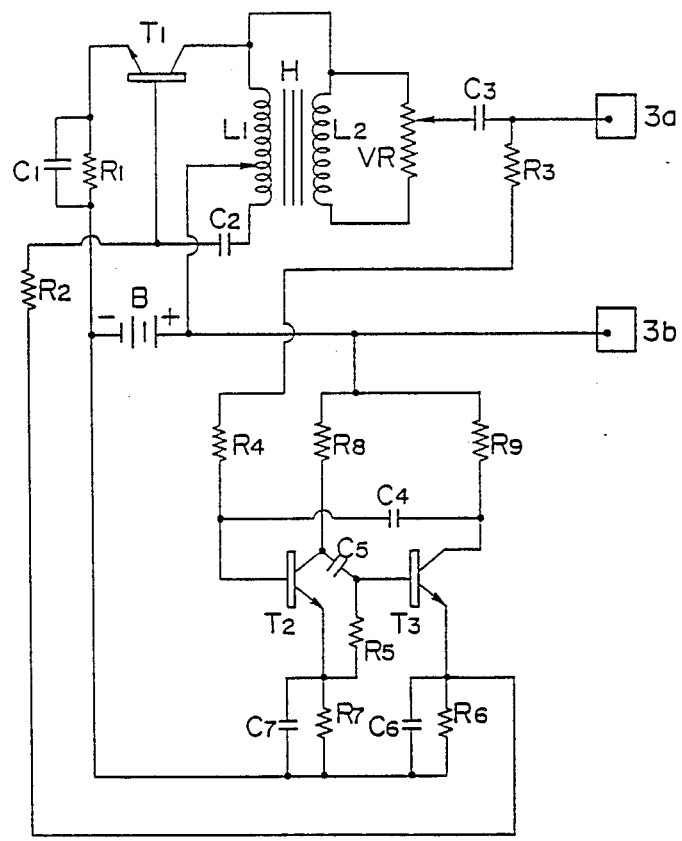
FIG. 2, the circuit of an embodiment according to the invention.

FIG. 2 is the circuit of an embodiment according to the invention using a multivibrator and a blocking oscillator respectively as the first and second oscillator circuits. In the circuit, when electrode pair (3a)(3b) is in connection with a load such as the subject's body, battery B energizes the multivibrator comprising transistors $T_2$ and $T_3$ respectively through electrode (3b), load, electrode (3a) and resistor $R_3$ so that the multivibrator initiates oscillation of the low-frequency square wave as shown in FIG. 3b. Capacitor $C_6$ and resistor $R_6$ are connected with the emitter of transistor $T_3$, and the output of the multivibrator is supplied to the base of transistor $T_1$ in the blocking oscillator through resistor $R_2$ from the emitter that becomes positive every half cycle. Transistor $T_1$ attains no oscillation when the output voltage of the multivibrator is zero and this renders the base voltage zero, but generates a diphasic action potential when the square wave comes to the positive region every half cycle. The output of the blocking oscillator is supplied to electrode (3a) through capacitor $C_3$, and the load such as the subject's body receives the diphasic action potential over a time period equal to the pulse width of the square wave at time intervals equal to the pulse interval. Thus, by controlling the frequency and/or voltage of the square wave with variable resistor VR, strong muscle contraction and relaxation can be attained by applying a relatively low therapeutic voltage.

Since removal of electrode pair (3a)(3b) suspends the supply of dc current to resistor $R_4$, oscillation of the multivibrator and blocking oscillator is stopped automatically. Thus, discharge of battery B is automatically suspended even when the subject forgets to switch it off.

Figure 4:
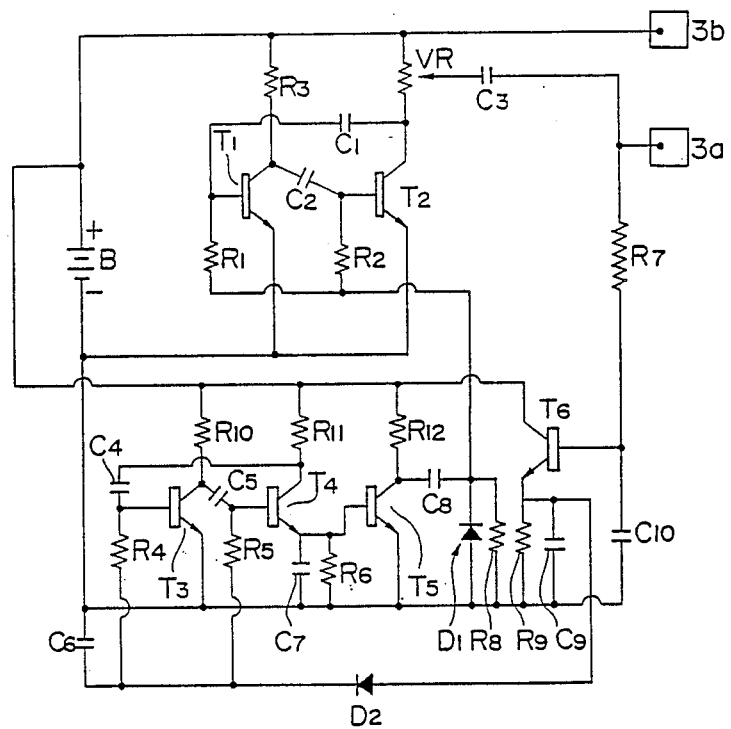
FIG. 4, the circuit of another embodiment according to the invention

The diphasic action potential wave can be attained by using a multivibrator as second oscillator circuit as shown in FIG. 4.

As described above, since the present invention is arranged in this way, natural, painless, strong muscle contraction and relaxation can be realized by applying a relatively small therapeutic voltage.

More particularly, the device having a second oscillator circuit, oscillation frequency of about 10–300 hertz, exerts a remarkable therapeutic effect when used while having a bath: At a frequency of 100 hertz or lower, preferably, 10–70 hertz, the device is effective in improvement or treatment of blood circulation, muscular strength, fatigue and hemorrhoids; and at a frequency of 100–300 hertz, in prevention of alopecia as well as in acceleration and regeneration of hair.

Furthermore, discharge of the battery in the device is automatically suspended if the subject forgets to switch it off because the device is not actuated when the electrode pair is not in connection with the load.

Having described specific embodiments of my invention, modifications and variations of my invention are possible in the light of the above teachings.

I claim:

1. A device to effect low-frequency electrotherapy to a subject's body with the body being an electrical load on the device, said device comprising
   a direct current source;
   a first electrode and a second electrode across which the electrical load of the body is applied during operation of the device;
   a first oscillator circuit connected to said direct current source through said first and second electrodes when the electrical load of the body is applied across said electrodes;
   said first oscillator circuit having an output connected to an input of a second oscillator circuit to said first electrode, for said first oscillator circuit to generate a low-frequency square wave voltage to the load across said electrodes;
   said second oscillator circuit having an output connected to said first electrode to generate a diphasic action potential to the load across said electrodes when the low-frequency square wave voltage generated by said first oscillator circuit is not zero;
   said second electrode connected with a return circuit common to said first and second oscillator circuits through said direct current source to actuate said first oscillator circuit only when the load of the body is applied across said electrodes.

2. The device of claim 1 further comprising
   variable resistor means to control the frequency of the low-frequency square wave voltage generated by said first oscillator circuit
   whereby the strength of said diphasic action potential across the load is controlled.

3. The device of claim 1 further comprising
   variable resistor means to control the voltage of the low-frequency square wave voltage generated by said first oscillator circuit
   whereby the strength of said diphasic action potential across the load is controlled.

4. The device of claim 1 wherein
   said first oscillation circuit is a multivibrator.

5. The device of claim 1 wherein
   said second oscillation circuit is a blocking oscillator.

6. The device of claim 1 wherein
   said second oscillation circuit is a multivibrator.

7. The device of claim 1 wherein
   said first oscillator circuit generates a low-frequency square wave voltage with a frequency in the range of 0.1–2 hertz.

8. The device of claim 1 wherein
   said second oscillator circuit generates a diphasic action potential with a frequency in the range of 10–300 hertz.

* * * * *